United States Patent [19]

Bhitiyakul et al.

[11] 4,320,745
[45] Mar. 23, 1982

[54] FIBER OPTICS LARYNGOSCOPE

[76] Inventors: Sumsak Bhitiyakul, c/o George Spector, 3615 Woolworth Bldg., 233 Broadway; George Spector, 3615 Woolworth Bldg., 233 Broadway, both of, New York, N.Y. 10007

[21] Appl. No.: 111,832

[22] Filed: Jan. 14, 1980

[51] Int. Cl.³ .............................................. A61B 1/26
[52] U.S. Cl. ...................................... 128/11; 128/16; 128/13
[58] Field of Search .................. 128/9, 10, 11, 12, 13, 128/15, 16, 17, 18

[56] References Cited

U.S. PATENT DOCUMENTS

| 2,240,402 | 4/1941 | Joroslow | 128/16 |
| 3,771,514 | 11/1973 | Huffman et al. | 128/11 |
| 4,037,588 | 7/1977 | Heckele | 128/11 |

Primary Examiner—Robert W. Michell
Assistant Examiner—Nancy A. B. Swisher

[57] ABSTRACT

A laryngoscope instrument for visual inspection of the laryngeal region of the oral cavity; including a bent blade of refractory material for insertion through a mouth and into the throat an outward end of the blade being bifurkated with an opaque shield between, the two tongues thus formed, one tongue aligning with an eyepiece for observation therethrough, and the other tongue aligning with an electric lamp for illuminating the observed region.

5 Claims, 2 Drawing Figures

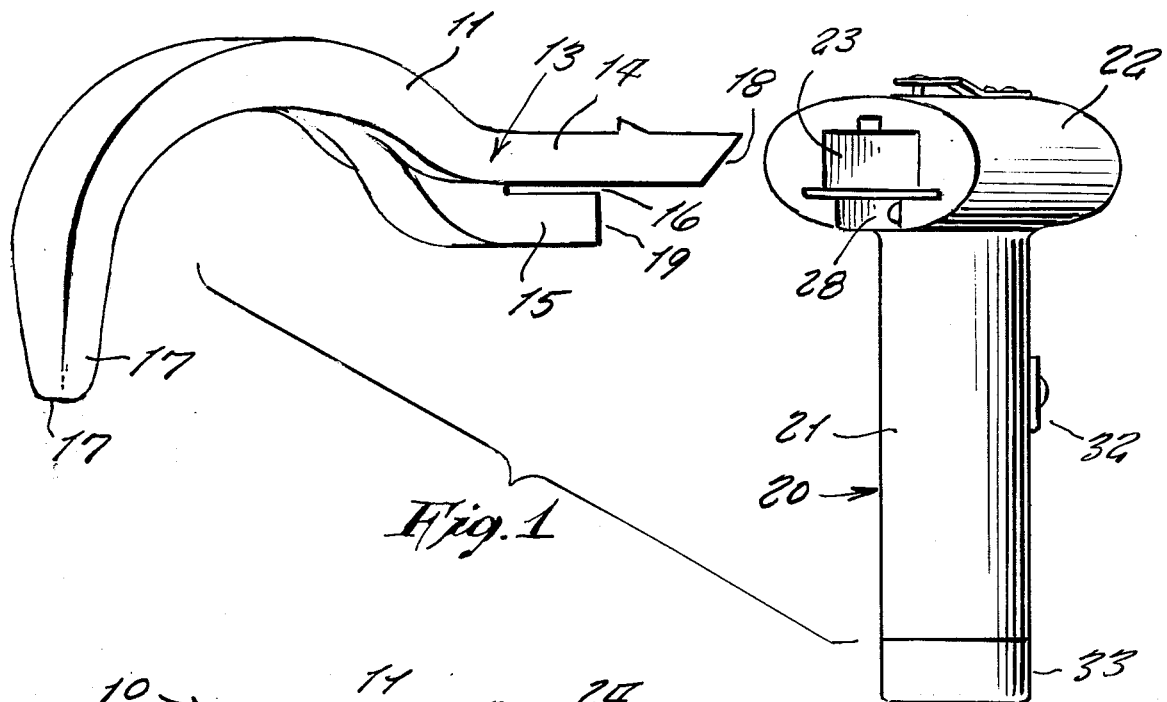
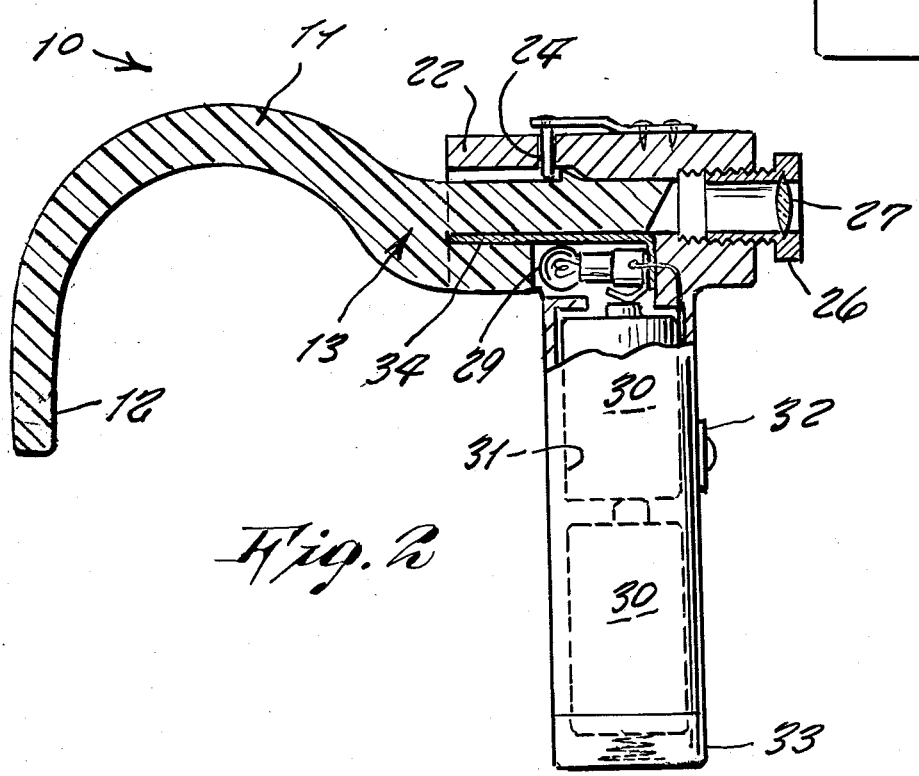

FIBER OPTICS LARYNGOSCOPE

This invention relates generally to laryngoscopes, such as are used for observation of the larngeal area of a patient, by a phycisian.

It is well known that numerous laryngoscopes have been developed in the past, and wherein an electric lamp is installed along the instrument blade so as to illuminate the observed area. However, such lamps, even if shielded from a rear side so as to prevent light glare toward the observer's eye, are objectionable, in view that the lamp intercepts with the line of sight and prevents a full viewing.

Accordingly, it is a principal object of the present invention wherein there is a fiber optics laryngoscope wherein the electric lamp does not intercept the line of sight between the observed region and the eyepiece, so that an improved injection is thus made possible.

Another object is to provide a fiber optics laryngoscope wherein the lamp is nevertheless still located adjacent the blade and closer to the observed area than the eyepiece, so that its illumination intensity is not decreased, such as in those instruments wherein the lamp is located farther away than the eyepiece.

FIG. 1 is a perspective view of the invention units shown separated.

FIG. 2 is a side cross sectional view thereof, shown assembled, and the invention including a base end of the blade being forked so one part thereof faces the lamp while the other leads to the observation window fitted with adjusted lens, and an opaque partition between the forked ends so to decrease light glare directly from the lamp to the observation window, thus resulting in a clearer visibility of the larynx tissue.

Referring now to the drawing in greater detail, the reference numeral 10 represents a fiber optics laryngoscope according to the present invention, wherein there is a blade 11 of a curved shaped so as to be insertable through a mouth and into a throat; the blade being extruded from a refractory material such as transparent thermoplastic lucite or the like so that light rays can be transmitted therethrough irregardless of the curvature of the longitudinal plane thereof. The end 12 of the blade is positioned within the larynx, while the opposite end 13 thereof extends outward of the patient's mouth.

In the present invention, the end 13 is bifurkated so as to form parallel tongues 14 and 15, with a space 16 therebetween. While all longitudinal surfaces are polished smooth, the end faces 17, 18 and 19 are such so that light rays and an observed image can pass therethrough. The blade is detachably securable in a handle 20.

The handle includes a cylindrical hand grip 21 for being grasped by a hand, one end of the hand grip being integral with a transverse sleeve 22 having an opening 23 therethrough and into which the blade end 13 is receivable. A spring biased detent pin 24 on the sleeve snaps behind a detent protrusion 25 formed on the blade, for retaining the blade from accidentally falling out.

An eyepiece 26 having a lens 27 is adjustably fitted on a threaded end portion of the opening 23 so as to align with face 18 and be adjustable for focusing.

A radially extending opening 28 in the sleeve contains an electric lamp 29 in electrical circuit with dry cell batteries 30 inside a chamber 31 within the handle and a manually operated switch 32 on a side of the handle. A removable end cap 33 on an end of the handle allows access for changing worn out batteries.

The lamp is mounted upon an L-shaped shield 34 made of opaque stiff material such as metal, and which closes the inward end of the radial opening 28. A protruding end of the shield, extending to a front end of the sleeve, thus fits into the space 16 when the blade is attached to the handle. The shield prevents lamp glare toward the eyepiece.

In operative use, the blade is inserted into the throat, the lamp is inserted into the throat, the lamp switch is turned on, and observation is then made into the eyepiece.

We claim the following:

1. A laryngoscope comprising a blade with a rear extension in combination with a handle in which said extension is mounted removably, said blade and extension being formed of light transmitting material, said extension including spaced tongues, one of which transmits light to said blade and the other tongue receives images from said blade, said handle having a viewer aligned with the said other tongue and a lamp aligned with the said one tongue.

2. A device as in claim 1 wherein the handle includes opaque means separating said tongues.

3. A device as in claim 2 wherein said tongues are parallel.

4. A device as in claim 3 wherein said handle includes a hollow downward portion adapted to receive batteries and providing a handhold, said handle including an upper portion including recesses for housing said lamp, receiving said spaced tongues and an adjustable viewer.

5. A device as in claim 4, said handle and extension including means for removably retaining said extension in said handle.

* * * * *